United States Patent [19]

Takizawa et al.

[11] 4,353,923

[45] Oct. 12, 1982

[54] PHARMACEUTICAL COMPOSITION CONTAINING A BENZOFURANCARBOXAMIDE DERIVATIVE AS THE ACTIVE INGREDIENT

[75] Inventors: Hiroshi Takizawa; Yoshimasa Oiji; Tatsuyuki Hirayama, all of Shizuoka, Japan

[73] Assignee: Kyowa Hakko Kogyo Co., Ltd., Tokyo, Japan

[21] Appl. No.: 284,377

[22] Filed: Jul. 17, 1981

[30] Foreign Application Priority Data

Aug. 1, 1980 [JP] Japan ................................. 55/105138

[51] Int. Cl.³ ............................................. A61K 31/34
[52] U.S. Cl. .................................................... 424/285
[58] Field of Search ........................................ 424/285

[56] References Cited

FOREIGN PATENT DOCUMENTS 50-4238 of 1975 Japan .

Primary Examiner—Stanley J. Friedman
Attorney, Agent, or Firm—Antonelli, Terry & Wands

[57] ABSTRACT

A pharmaceutical composition, specifically a muscle relaxant acting at the same time as an anti-inflammatory and analgesic agent which composition comprises pharmaceutically acceptable carrier(s) and a benzo[b]furancarboxamide derivative represented by the general formula:

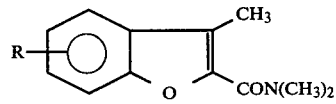

wherein R represents a halogen atom, an alkyl group having 1–5 carbon atoms or an alkoxy group having 1–5 carbon atoms.

12 Claims, No Drawings

PHARMACEUTICAL COMPOSITION CONTAINING A BENZOFURANCARBOXAMIDE DERIVATIVE AS THE ACTIVE INGREDIENT

FIELD OF THE INVENTION

The present invention relates to a pharmaceutical composition containing as the active ingredient a benzo[b]furancarboxamide derivative. The derivatives have a strong muscle relaxant activity and an anti-inflammatory and analgesic activity.

DESCRIPTION OF PRIOR ART

Japanese Published Unexamined Patent Application No. 4238/1975 discloses that a benzo[b]furancarboxamide derivative represented by the following general formula has a herbicidal activity.

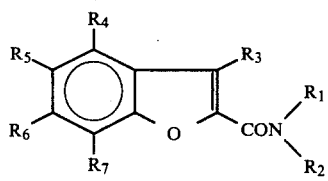

In the formula, $R_1$ represents a hydrogen atom, an alkyl group having 1–5 carbon atoms or a methoxy group; $R_2$ represents a hydrogen atom or an alkyl group having 1–3 carbon atoms; $R_3$ represents a hydrogen atom or a methyl group; and $R_4$, $R_5$, $R_6$ and $R_7$ represent a hydrogen atom, a halogen atom, an alkyl group having 1–3 carbon atoms or a methoxy group and at least three of $R_4$, $R_5$, $R_6$ and $R_7$ are a hydrogen atom. However, there is neither disclosure nor suggestion in the application that compounds of the above general formula have an activity as medicine.

The present inventors have studied pharmacological activities of various benzo[b]furan derivatives, have found that specific benzo[b]furancarboxamide derivatives, some of which fall within the definition of the above general formula in Japanese Published Unexamined Patent Application No. 4238/1975, have a muscle relaxant activity and an anti-inflammatory and analgesic activity, and have completed the present invention.

DESCRIPTION OF THE INVENTION

The present invention relates to a pharmaceutical composition which comprises pharmaceutically acceptable carrier(s) and a benzo[b]furancarboxamide derivative represented by the general formula (I):

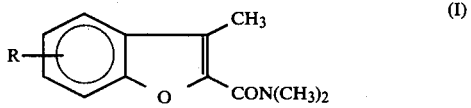

wherein R represents a halogen atom, an alkyl group having 1–5 carbon atoms or an alkoxy group having 1–5 carbon atoms [hereinafter referred to as Compound (I)].

In the above definition, examples of the halogen atom include fluorine, chlorine, bromine and iodine, examples of the alkyl group include methyl, ethyl, n-propyl, i-propyl, n-butyl and n-pentyl, and examples of the alkoxy group include methoxy, ethoxy, n-propoxy, isopropoxy, n-butoxy and n-pentoxy.

Examples of Compound (I) are as follows:

| | Referred to as |
|---|---|
| 4-Chloro-N,N,3-trimethyl-benzo[b]furan-2-carboxamide | Compound (A) |
| 6-Chloro-N,N,3-trimethyl-benzo[b]furan-2-carboxamide | Compound (B) |
| 7-Chloro-N,N,3-trimethyl-benzo[b]furan-2-carboxamide | Compound (C) |
| 5-Fluoro-N,N,3-trimethyl-benzo[b]furan-2-carboxamide | Compound (D) |
| N,N,3,5-Tetramethylbenzo-[b]furan-2-carboxamide | Compound (E) |
| 5-Methoxy-N,N,3-trimethyl-benzo[b]furan-2-carboxamide | Compound (F) |
| 5-Chloro-N,N,3-trimethyl-benzo[b]furan-2-carboxamide | Compound (G) |

Compound (I) has a low toxicity, a strong muscle relaxant activity, and an anti-inflammatory and analgesic activity. When the compounds are used as medicine, that is, as muscle relaxant, anti-inflammatory agent or analgesic agent, they are usually administered in an amount of 100–1000 mg per day per adult either in one dose or in two or three doses. More in detail, when the compounds are used for muscle relaxation alone or for muscle relaxation and at least one of anti-inflammation and analgesic purpose, they are orally administered usually in an amount of 200–600 mg per day per adult either in one dose or in two or three doses. In intravenous and subcutaneous administration, the dose is respectively reduced to about one tenth and one fifth of that in oral administration. When the compounds are used mainly for anti-inflammation, they are orally administered usually in an amount of 600–900 mg per day per adult either in one dose or in two or three doses.

The compounds are administered in the form of tablets, granules, powder, capsules, syrup, ointment, cream, injection or the like prepared in a conventional manner depending upon the purpose and method of administration. For example, in a tablet form, tablets containing 50–150 mg of active ingredient per tablet are preferably used. In preparing tablets, an excipient (e.g., lactose, glucose, sucrose, mannitol, methylcellulose, etc.), a disintegrator (e.g., starch, sodium alginate, carboxymethylcellulose calcium, crystalline cellulose, etc.), a lubricant (e.g., magnesium stearate, talc, etc.), a binder (e.g., gelatin, polyvinyl alcohol, polyvinyl pyrrolidone, hydroxypropylcellulose, methylcellulose, etc.), a surfactant (e.g., fatty acid ester of sucrose, fatty acid ester of sorbitol, etc.) and the like are used in a conventional manner. In preparing granules, an excipient (e.g., lactose, sucrose, etc.), a disintegrator (e.g., starch, etc.), a binder (e.g., gelatin) and the like are used in a conventional manner. In preparing powder, an excipient (e.g., lactose, mannitol, etc.) and the like are used in a conventional manner. In a capsule form, capsules containing 50–150 mg of active ingredient per capsule are preferably used. In preparing capsules, gelatin, water, sucrose, Arabic gum, sorbitol, glycerin, crystalline cellulose, magnesium stearate, talc, etc. are used in a conventional manner. In preparing syrup, sugar (e.g., sucrose, etc.), water, ethanol, etc. are used in a conventional manner. In preparing ointment, ointment base (e.g., vaseline, liquid paraffin, lanolin, macrogol, etc.), emulsifying agent (e.g., sodium lauryl sulfate, benzalkonium chloride, monoaliphatic acid ester of sorbitan, carboxymethylcellulose sodium, Arabic gum, etc.) and the like are used in a conventional manner.

Ointment is a form adopted mainly for anti-inflammation. It is preferable that ointment containing Compound (I) at a concentration of 0.05–5% (w/w) is applied 1–3 times a day.

In preparing injection, solvent (e.g., water, physiological sodium chloride solution, vegetable oil such as olive oil and peanut oil, ethyl oleate, propylene glycol, etc.), a solubilizing agent (e.g., sodium benzoate, sodium salicylate, urethane, etc.), a tonicity agent (e.g., sodium chloride, glucose, etc.), a preservative (e.g., phenol, cresol, an ester of p-oxybenzoic acid, chlorobutanol, etc.), an anti-oxidant (e.g., ascorbic acid, sodium pyrosulfite, etc.) and the like are used in a conventional manner.

Compound (I) can be easily prepared by combinations of various known methods for organic synthesis. Specifically, Compound (I) can be prepared by a similar method to that described in Japanese Published Unexamined Patent Application No. 18975/1981 and U.S. patent application Ser. No. 172,949 filed on July 28, 1980. For example, Compound (I) can be prepared from a benzo[b]furancarboxylic acid compound represented by the general formula (II):

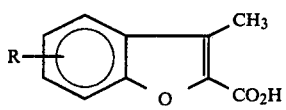

(wherein R has the same significance as defined above) [hereinafter referred to as Compound (II); Typical method for preparation thereof is disclosed in Organic Synthesis Collective volume 4, 590] according to the following representative methods (A to I methods).

[A method]: a method which comprises converting Compound (II) to an acyl halide and reacting the acyl halide with dimethylamine

[B method]: a method which comprises directly reacting Compound (II) with dimethylamine in the presence of a coupling agent such as N,N'-dicyclohexylcarbodiimide (hereinafter referred to as DCC)

[C method]: a method which comprises preparing an active ester from Compound (II) and N-hydroxysuccinimide (hereinafter referred to as NOS), etc. and reacting the active ester with dimethylamine

[D method]: a method which comprises preparing a mixed acid anhydride from Compound (II) and ethyl chlorocarbonate, etc. and reacting the mixed acid anhydride with dimethylamine

[E method]: a method which comprises preparing an acid azide by converting Compound (II) to an acyl halide and reacting the acyl halide with sodium azide or by converting Compound (II) to an acid hydrazide and reacting the acid hydrazide with nitrous acid, and reacting the acid azide with dimethylamine

[F method]: a method which comprises heating a solution of Compound (II) in hexamethylphosphoramide [Reference: Chem. Ind. (London) 1966, 1529]

[G method]: a method which comprises heating Compound (II) with dimethylformamide solution of phosphorus pentoxide [Reference: Monatsh Chem. 99, 1799 (1968)]

[H method]: a method which comprises heating an alkali salt of Compound (II) with dimethylcarbamoyl chloride for decarboxylation [Reference: J. Org. Chem. 28, 232 (1963)]

[I method]: a method which comprises converting Compound (II) to an acyl halide and heating the acyl halide with dimethylformamide [Reference: J. Amer. Chem. Soc., 76, 1372 (1954)]

Further, Compound (I) can also be readily prepared according to a method which comprises preparing a 2-phenoxyacetoacetamide compound represented by the general formula (III):

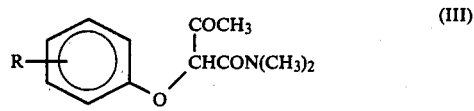

(wherein R has the same significance as defined above) [hereinafter referred to as Compound (III)] from a corresponding phenol compound and 2-chloro-N,N-dimethylacetoacetamide (Reference: U.S. Pat. No. 3,284,500) and cyclizing Compound (III) [K method], or according to a method which comprises preparing a (2-acetyl)phenoxyacetamide compound represented by the general formula (IV):

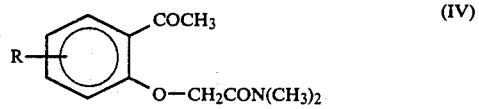

(wherein R has the same significance as defined above) [hereinafter referred to as Compound (IV)] from a corresponding 2-acetylphenol compound and N,N-dimethylchloroacetamide (Reference: Beilsteins Handbuch der Organischen Chemie 4, I, 329) and cyclizing Compound (IV) [L method] (Reference: Ger. Offen. No. 1,932,933).

Representative A method is explained in detail below.

(A method)

Compound (II) is reacted with an inorganic halogen compound such as phosphoryl chloride, thionyl chloride, phosphorus pentachloride and phosphorus trichloride to obtain an acyl halide. The reaction may be carried out without solvent or in an inert solvent such as methylene chloride, chloroform, carbon tetrachloride, benzene, toluene, xylene, diethyl ether, diisopropyl ether, tetrahydrofuran, pyridine and triethylamine. Though specific catalysts are unnecessary for the reaction in general, the reaction may be promoted by addition of zinc chloride, pyridine, iodine, triethylamine, etc. in a catalytic amount to equimolar amount. The reaction is carried out at room temperature to the boiling point of the inorganic halogen compound or the solvent and is completed in 30 minutes to 5 hours. Reaction of the acyl halide with dimethylamine may be carried out by blowing gaseous dimethylamine into a solution of the acyl halide in an inert solvent which is selected from those described above, or by adding the acyl halide to a solution of dimethylamine in water or an inert solvent. It is preferable to use dimethylamine in an amount of 2 moles or more per mole of the acyl halide in order to remove hydrohalogenic acid as a by-product. Alternatively, the reaction may be carried out in the presence of a tertiary amine such as triethylamine or using pyridine, etc. as a solvent for the same purpose. As the reaction proceeds very rapidly accompanying much generation of heat, the proper reaction temperature is −30° C. to room temperature. Time needed for mixing dimethylamine with the acyl halide is sufficient as the reaction time.

Isolation of thus obtained Compound (I) from the reaction mixture is carried out by the conventional method in organic chemistry. Preferably, the isolation is carried out by column chromatography or recrystallization.

The present invention is illustrated in more detail by the following examples and reference examples.

EXAMPLE 1

Acute toxicity test

In this example, 3-7 male dd mice weighing 20±1 g were used as one group. Each drug was suspended in a 0.3% CMC solution and orally administered. After the administration, number of dead animals was counted for 7 days to determine $LD_{50}$ value. The result is shown in Table 1. As the reference drugs, mepirizole and benzydamine hydrochloride were dissolved in water and orally administered. The drugs and the reference drugs were also administered in the same manner as above in Examples 2-5.

EXAMPLE 2

Muscle relaxant activity

In this example, 5 male dd mice weighing 20±1 g were used as one group. Prior to the experiments, mice were placed on the rod having a diameter of 3 cm and rotating at 5 r.p.m. in the reverse direction of the rotation. The mice which did not fall for 3 minutes or more were selected and used for the experiments. The drugs were orally administered and the muscle relaxant activity with the passage of time was examined by the following tests.

Slant test: Each mouse was placed on a wire net inclined at an angle of 45° to observe whether it falls or not.

Traction test: Forefeet of the same mouse were placed on a wire to observe whether it falls or not.

Rotating rod test: The same mouse was placed on the rotating rod to observe whether it falls or not within 2 minutes.

In each test, the drug was considered to have a muscle relaxant activity when the mouse fell. The results are shown in Table 2.

TABLE 2

| Compound | Slant test | | | | Rotating rod test | | | | Traction test | | | |
|---|---|---|---|---|---|---|---|---|---|---|---|---|
| | Dose mg/kg p.o. | \multicolumn{3}{c}{Number of dropped mice} | | Dose mg/kg p.o. | Number of dropped mice | | | Dose mg/kg p.o. | Number of dropped mice | | |
| | | 1 | 2 | 3 hr* | | 1 | 2 | 3 hr* | | 1 | 2 | 3 hr* |
| (A) | 300 | 4 | 3 | 3 | 75 | 3 | 2 | 1 | 75 | 3 | 0 | 0 |
| | | | | | 150 | 5 | 5 | 2 | 150 | 5 | 3 | 1 |
| (B) | 300 | 5 | 5 | 5 | 75 | 5 | 4 | 4 | 75 | 3 | 4 | 2 |
| | | | | | 150 | 5 | 5 | 5 | 150 | 5 | 5 | 5 |
| (C) | 50 | 5 | 4 | 1 | 25 | 3 | 1 | 0 | 25 | 0 | 0 | 0 |
| | 100 | 5 | 5 | 5 | 50 | 5 | 5 | 2 | 50 | 5 | 4 | 1 |
| | | | | | 100 | 5 | 5 | 5 | 100 | 5 | 5 | 5 |
| (D) | 150 | 4 | 4 | 1 | 50 | 0 | 0 | 0 | 50 | 0 | 0 | 0 |
| | | | | | 75 | 3 | 1 | 0 | 75 | 2 | 1 | 0 |
| | | | | | 100 | 5 | 3 | 1 | 100 | 2 | 1 | 0 |
| (E) | 150 | 1 | 0 | 0 | 150 | 5 | 5 | 3 | 150 | 4 | 3 | 2 |
| | 300 | 3 | 2 | 1 | 150 | 1 | 0 | 0 | 150 | 0 | 0 | 0 |
| | | | | | 300 | 4 | 2 | 2 | 300 | 3 | 1 | 1 |
| (F) | 300 | 4 | 2 | 1 | 150 | 1 | 0 | 0 | 150 | 1 | 0 | 0 |
| | | | | | 300 | 5 | 5 | 3 | 300 | 5 | 3 | 1 |
| (G) | 150 | 3 | 2 | 2 | 75 | 3 | 1 | 1 | 75 | 1 | 1 | 1 |
| | 300 | 5 | 5 | 5 | 150 | 5 | 4 | 3 | 150 | 3 | 3 | 2 |
| Mepirizole | 150 | 3 | 1 | 0 | 150 | 5 | 1 | 0 | 150 | 2 | 0 | 0 |
| Benzydamine hydrochloride | 300 | 4 | 2 | 0 | 300 | 5 | 3 | 2 | 300 | 5 | 1 | 0 |

*Time after the administration of drug.

TABLE 1

| Compound | $LD_{50}$ mg/kg p.o. |
|---|---|
| (A) | >1000 |
| (B) | 500-1000 |
| (C) | >1000 |
| (D) | 700-1000 |
| (E) | >1000 |
| (F) | >1000 |
| (G) | >1000 |
| Mepirizole | 500-1000 |
| Benzydamine hydrochloride | 500-1000 |

EXAMPLE 3

Anticonvulsant activity

Anticonvulsant activity was examined according to maximal electroshock convulsion test.

In this experiment, 10 male dd mice weighing 23±1 g were used as one group. Each drug was orally administered to the animals. Sixty minutes after the administration, an electric current (2000 V, 50 mA) was applied to both eyes of the mouse for 0.2 second. Drug activity was judged according to whether tonic extensor seizures were observed or not. The results are shown in Table 3.

TABLE 3

| Compound | Maximal electroshock convulsion test | |
|---|---|---|
| | Dose mg/kg p.o. | Inhibition ratio (%) |
| (A) | 25 | 10 |
| | 50 | 30 |
| | 75 | 80 |
| (B) | 25 | 0 |
| | 50 | 40 |
| | 75 | 60 |
| (C) | 25 | 40 |
| | 50 | 66.7 |
| | 75 | 80 |
| | 100 | 100 |
| (D) | 50 | 10 |
| | 75 | 40 |
| | 100 | 90 |
| (E) | 150 | 10 |
| | 300 | 57.1 |
| (F) | 150 | 30 |
| | 300 | 100 |
| (G) | 50 | 0 |
| | 75 | 40 |
| | 100 | 100 |
| Mepirizole | 100 | 20 |
| | 150 | 85.7 |
| | 300 | 100 |
| Benzydamine hydrochloride | 50 | 35 |
| | 75 | 90 |
| | 100 | 100 |
| | 300 | 100 |

EXAMPLE 4

Analgesic activity

In this experiment, 10 male dd mice weighing 20±1 g were used as one group for examination of analgesic activity. Sixty minutes after oral administration of each drug to each animal, 0.2 ml of a 0.7% acetic acid solution was intraperitoneally administered to the animal. Starting 10 minutes after the administration of acetic acid, the number of writhes occurred in 10 minutes was counted. Average number of writhes and inhibition ratio in comparison with control group were calculated. The results are shown in Table 4.

TABLE 4

| Compound | Dose mg/kg p.o. | Inhibition ratio (%) |
|---|---|---|
| (A) | 50 | 60.6 |
| | 150 | 100.0 |
| (B) | 50 | 34.9 |
| | 150 | 95.4 |
| (C) | 50 | 85.3 |
| | 150 | 100.0 |
| (D) | 50 | 44.2 |
| | 150 | 95.4 |
| (E) | 150 | 22.6 |
| (F) | 150 | 11.0 |
| (G) | 150 | 91.4 |
| Mepirizole | 50 | 30.4 |
| | 200 | 84.7 |
| Benzydamine hydrochloride | 50 | 0 |
| | 200 | 83.7 |

EXAMPLE 5

Anti-inflammatory activity (Carrageenin edema method)

In this experiment, 5 male Wistar rats weighing 140±10 g were used as one group. Sixty minutes after oral administration of each drug to each animal, 0.1 ml of a 1% carrageenin solution as a phlogistic agent was injected into the plantar surface of the right hind paw of the animal to induce inflammation. The volume of the paw was measured before and 3 hours after the injection of the phlogistic agent. Swelling ratio and inhibition ratio in comparison with control group were calculated. The results were shown in Table 5.

TABLE 5

| Compound | Dose mg/kg p.o. | Inhibition ratio (%) |
|---|---|---|
| (A) | 150 | 33.4 |
| (B) | 150 | 39.8 |
| (C) | 150 | 35.1 |
| | 300 | 57.8 |
| (D) | 150 | 34.0 |
| (E) | 150 | 14.7 |
| (F) | 150 | 0 |
| (G) | 150 | 45.7 |
| Mepirizole | 100 | 29.2 |
| | 200 | 47.0 |
| Benzydamine hydrochloride | 100 | 14.4 |
| | 200 | 23.5 |

EXAMPLE 6

Tablet

In this example, 10,000 tablets having the following composition are prepared according to a conventional method. Each tablet contains 50 mg of active ingredient.

| | |
|---|---|
| 7-Chloro-N,N,3-trimethylbenzo[b]furan-2-carboxamide | 500 g |
| Lactose | 343 g |
| Carboxymethylcellulose calcium | 93 g |
| Magnesium stearate | 4 g |
| Talc | 8 g |
| Polyvinyl alcohol | 25 g |
| Methylcellulose | 25 g |
| Glycerin | 2 g |
| Tar pigment | quantum sufficient |

EXAMPLE 7

Powder

Powders having the following composition are prepared according to a conventional method.

| | |
|---|---|
| 6-Chloro-N,N,3-trimethylbenzo[b]furan-2-carboxamide | 150 g |
| D-Mannitol | 850 g |

EXAMPLE 8

Capsule

Capsules having the following composition are prepared according to a conventional method.

| | |
|---|---|
| 5-Fluoro-N,N,3-trimethylbenzo[b]furan-2-carboxamide | 100 mg per capsule |
| Crystalline cellulose | 30 mg per capsule |
| Magnesium stearate | 3.6 mg per capsule |
| Talc | 3.6 mg per |

REFERENCE EXAMPLE 1

Preparation of 7-chloro-N,N,3-trimethylbenzo[b]furan-2-carboxamide [Compound (C)]:

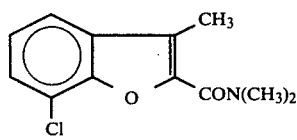

In this reference example, 31.6 g of 7-chloro-3-methylbenzo[b]furan-2-carboxamide is added to 100 ml of toluene, 30 ml of thionyl chloride is added thereto and the mixture is refluxed under heating for 2 hours. After completion of the reaction, the mixture is concentrated under reduced pressure and the residue is dissolved in 400 ml of anhydrous tetrahydrofuran. The solution is added dropwise to a mixed solution of 150 ml of 50% aqueous dimethylamine solution and 200 ml of tetrahydrofuran under ice-cooling over a period of 30 minutes. After stirring at room temperature for 30 minutes to complete the reaction, the reaction mixture is concentrated under reduced pressure and 300 ml each of water and chloroform is added to the residue. The water layer is adjusted to pH 11.0 and then the chloroform layer is separated. The chloroform solution is dehydrated and concentrated under reduced pressure to obtain 34.8 g of crude crystals in a crude yield of 98%. The crude crystals are recrystallized from 150 ml of n-hexane to obtain 27.7 g of purified crystals in a recrystallization yield of 80%.

The crystals have the following physical properties and are identified as the desired 7-chloro-N,N,3-trimethylbenzo[b]furan-2-carboxamide.

Melting point: 67°–69° C.

IR spectrum (KBr tablet, $cm^{-1}$): 2920, 1630, 1605, 1410, 1270, 890.

NMR spectrum ($CCl_4$, δ value, ppm): 2.40(s, 3H), 3.14(s, 6H), 6.9–7.5(m, 3H).

Elementary analysis (as $C_{12}H_{12}ClNO_2$):

|  | C (%) | H (%) | N (%) |
| --- | --- | --- | --- |
| Calculated | 60.64 | 5.09 | 5.89 |
| Found | 60.67 | 4.88 | 6.01 |

The above preparation method is one of the representative specific embodiments of A method.

REFERENCE EXAMPLE 2

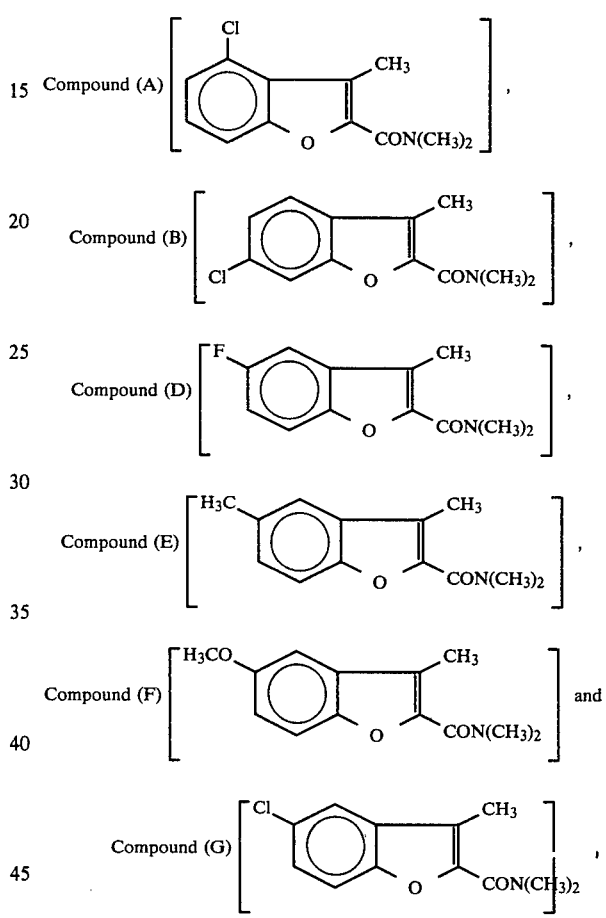

are synthesized in a similar manner as described in Reference Example 1. Amount of the used starting compounds, solvent for purification and yield are illustrated in Table 6. Physical properties of the obtained compounds are shown below.

TABLE 6

| Compound No. | Starting carboxylic acid (Used amount) | Thionyl chloride | 50% Aqueous dimethylamine solution | Amount of crude product (Crude yield) | Method for purification | Amount of purified product (Purification yield) |
| --- | --- | --- | --- | --- | --- | --- |
| (A) | 4-Chloro-3-methyl-benzo[b]furan-2-carboxylic acid 21.1 g | 20 ml | 100 ml | 20.2 g (85%) | Recrystallization n-Hexane 110 ml | 14.3 g (71%) |
| (B) | 6-Chloro-3-methyl-benzo[b]furan-2-carboxylic acid 16.5 g | 10 ml | 50 ml | 11.3 g (95%) | Recrystallization n-Hexane 90 ml Toluene 40 ml | 10.2 g (90%) |
| (D) | 5-Fluoro-3-methyl-benzo[b]furan-2-carboxylic acid | 10 ml | 50 ml | 10.1 g (91%) | Recrystallization n-Hexane 100 ml | 5.6 g (55%) |

TABLE 6-continued

| Compound No. | Starting carboxylic acid (Used amount) | Thionyl chloride | 50% Aqueous dimethylamine solution | Amount of crude product (Crude yield) | Method for purification | Amount of purified product (Purification yield) |
|---|---|---|---|---|---|---|
| (E) | 3,5-Dimethyl-benzo[b]furan-2-carboxylic acid 19.0 g | 20 ml | 100 ml | 19.3 g (89%) | Silica gel column chromatography (Toluene:Triethylamine = 30:1) | 13.1 g (68%) |
| (F) | 5-Methoxy-3-methyl-benzo[b]furan-2-carboxylic acid 20.6 g | 20 ml | 100 ml | 18.7 g (80%) | Silica gel column chromatography (Toluene:ethyl acetate = 10:1) | 11.2 g (60%) |
| (G) | 5-Chloro-3-methyl-benzo[b]furan-2-carboxylic acid 10.5 g | 10 ml | 50 ml | 10.7 g (90%) | Recrystallization n-Hexane 80 ml | 7.5 g (70%) |

PHYSICAL PROPERTIES OF EACH COMPOUND

Compound (A)

Melting point: 55°–57° C.
IR spectrum (KBr tablet, cm$^{-1}$): 2920, 1630, 1605, 1410, 1180, 940.
NMR spectrum (CDCl$_3$, δ value, ppm): 2.57(s, 3H), 3.06(s, 6H), 7.0–7.4(m, 3H).

Elementary analysis (as C$_{12}$H$_{12}$ClNO$_2$):

|  | C (%) | H (%) | N (%) |
|---|---|---|---|
| Calculated | 60.64 | 5.09 | 5.89 |
| Found | 60.71 | 5.31 | 5.60 |

Compound (B)

Melting point: 116°–118° C.
IR spectrum (KRr tablet, cm$^{-1}$): 2930, 1630, 1605, 1420, 1120, 825.
NMR spectrum (CDCl$_3$, δ value, ppm): 2.38(s, 3H), 3.11(s, 6H), 7.0–7.5(m, 3H).

Elementary analysis (as C$_{12}$H$_{12}$ClNO$_2$):

|  | C (%) | H (%) | N (%) |
|---|---|---|---|
| Calculated | 60.64 | 5.09 | 5.89 |
| Found | 60.83 | 5.18 | 5.75 |

Compound (D)

Melting point: 34°–35° C.
IR spectrum (KBr tablet, cm$^{-1}$): 2930, 1630, 1450, 1400, 1180, 820.
NMR spectrum (CCl$_4$, δ value, ppm): 2.34(s, 3H), 3.07(s, 6H), 6.8–7.5(m, 3H).

Elementary analysis (as C$_{12}$H$_{12}$FNO$_2$):

|  | C (%) | H (%) | N (%) |
|---|---|---|---|
| Calculated | 65.15 | 5.47 | 6.33 |
| Found | 65.6 | 5.45 | 6.51 |

Compound (E)

IR spectrum (NaCl cell, cm$^{-1}$): 2920, 1630, 1400, 1265, 1075, 800.
NMR spectrum (CCl$_4$, δ value, ppm): 2.37(s, 6H), 3.04(s, 6H), 6.9–7.4(m, 3H).

Elementary analysis (as C$_{13}$H$_{15}$NO$_2$):

|  | C (%) | H (%) | N (%) |
|---|---|---|---|
| Calculated | 71.86 | 6.96 | 6.45 |
| Found | 71.59 | 7.00 | 6.61 |

Compound (F)

IR spectrum (NaCl cell, cm$^{-1}$): 2930, 1630, 1480, 1400, 1210, 830.
NMR spectrum (CCl$_4$, δ value, ppm): 2.36(s, 3H), 3.06(s, 6H), 3.74(s, 3H), 6.7–7.4(m, 3H).

Elementary analysis (as C$_{13}$H$_{15}$NO$_3$):

|  | C (%) | H (%) | N (%) |
|---|---|---|---|
| Calculated | 66.94 | 6.48 | 6.00 |
| Found | 66.98 | 6.52 | 5.93 |

Compound (G)

Melting point: 57°–59° C.
IR spectrum (KBr tablet, cm$^{-1}$): 2920, 1610, 1565, 1430, 1085, 805.
NMR spectrum (CCl$_4$, δ value, ppm): 2.36(s, 3H), 3.08(s, 6H), 7.2–7.6(m, 3H)

Elementary analysis (as C$_{12}$H$_{12}$ClNO$_2$):

|  | C (%) | H (%) | N (%) |
|---|---|---|---|
| Calculated | 60.64 | 5.09 | 5.89 |
| Found | 60.39 | 5.08 | 5.84 |

What is claimed is:

1. A muscle-relaxing, anti-inflammatory or analgesic composition which comprises at least one pharmaceutically acceptable carrier and an effective amount of a benzo[b]furancarboxamide compound represented by the general formula:

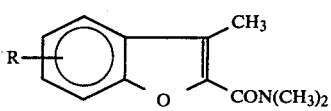

(I)

wherein R represents a halogen atom, an alykyl group having 1–5 carbon atoms or an alkoxy group having 1–5 carbon atoms to provide therapeutic activity to said composition.

2. A composition according to claim 1 wherein the effective amount is sufficient to provide muscle relaxant activity.

3. A composition according to claim 1 wherein the effective amount is sufficient to provide anti-inflammatory activity.

4. A composition according to claim 1 wherein the effective amount is sufficient to provide analgesic activity.

5. A composition according to claim 1, wherein said composition is in an administrable form of a tablet, capsule, powder, granules, syrup, ointment, cream or injection solution.

6. A composition according to claim 1 wherein said compound is 4-chloro-N,N,3-trimethylbenzo[b]furan-2-carboxamide.

7. A composition according to claim 1 wherein said compound is 6-chloro-N,N,3-trimethylbenzo[b]furan-2-carboxamide.

8. A composition according to claim 1 wherein said compound is 7-chloro-N,N,3-trimethylbenzo[b]furan-2-carboxamide.

9. A composition according to claim 1 wherein said compound is 5-fluoro-N,N,3-trimethylbenzo[b]furan-2-carboxamide.

10. A composition according to claim 1 wherein said compound is N,N,3,5-tetramethylbenzo[b]furan-2-carboxamide.

11. A composition according to claim 1 wherein said compound is 5-methoxy-N,N,3-trimethylbenzo[b]furan-2-carboxamide.

12. A composition according to claim 1 wherein said compound is 5-chloro-N,N,3-trimethylbenzo[b]furan-2-carboxamide.

* * * * *